United States Patent [19]

Fishman

[11] Patent Number: 4,673,106
[45] Date of Patent: Jun. 16, 1987

[54] DISPENSER FOR RETAINING TOOTHBRUSH AND FLOSS

[75] Inventor: Steven Fishman, Edison, N.J.

[73] Assignee: Colgate-Palmolive Company, New York, N.Y.

[21] Appl. No.: 790,510

[22] Filed: Oct. 23, 1985

[51] Int. Cl.⁴ ............................................. B65D 25/38
[52] U.S. Cl. ..................... 222/80; 222/130; 222/192; 222/391; 132/79 B; 132/79 E
[58] Field of Search ................ 222/93, 105, 106, 130, 222/191, 192, 391, 80; 132/79 B, 79 E, 92 R, 92 A

[56] References Cited

U.S. PATENT DOCUMENTS

| | | | |
|---|---|---|---|
| 811,370 | 1/1906 | Brush | 132/79 E |
| 1,492,836 | 5/1924 | Decker | 132/92 R |
| 1,501,656 | 7/1924 | Gilda | 222/93 |
| 3,155,279 | 11/1964 | Ferguson | 222/93 |
| 3,586,212 | 6/1971 | Tzouras et al. | 222/93 |
| 4,421,255 | 12/1983 | Czech | 222/391 X |
| 4,508,239 | 4/1985 | Rozzen | 222/93 X |
| 4,522,317 | 6/1985 | Goncalves | 222/391 |

Primary Examiner—Joseph J. Rolla
Assistant Examiner—Frederick R. Handren
Attorney, Agent, or Firm—Powell L. Sprunger

[57] ABSTRACT

A dispenser comprising, a container having a chamber for retaining a flowable material, and a nozzle defining an outlet orifice. The dispenser has a device for pumping the material through the orifice. The dispenser has a cap having an outwardly directed tab having an opening to receive a toothbrush. The dispenser has a spool rotatably received in a hollow lower base of the container, and an elongated strand of floss wound upon the spool and extending through an opening in the base.

5 Claims, 4 Drawing Figures

DISPENSER FOR RETAINING TOOTHBRUSH AND FLOSS

BACKGROUND OF THE INVENTION

The present invention relates to dispensers for a flowable material, such as toothpaste.

Conventionally, toothpaste has been sold in squeezable tubes. Recently, dispensers for toothpaste have been introduced in which the toothpaste is pumped from a chamber through an outlet orifice. Although these dispensers work satisfactorily, it is desirable to provide convenient access for devices to clean the teeth in conjunction with the toothpaste. Dispensers are disclosed in U.S. Pat. Nos. 4,437,591 and 4,461,403, incorporated herein by reference.

SUMMARY OF THE INVENTION

A principal feature of the present invention is the provision of an improved dispenser for a flowable material.

The dispenser of the present invention comprises, a container having a wall defining an elongated chamber to retain a flowable material, such as toothpaste, with a nozzle adjacent an upper portion of the chamber defining an outlet orifice, and a hollow lower base having an opening. The dispenser has a cap releasably secured to an upper portion of the container to close the nozzle.

A feature of the present invention is that the cap has an outwardly directed tab having an opening to receive a toothbrush.

Thus, a feature of the present invention is that the toothbrush is retained for convenient use for the toothpaste.

Another feature of the present invention is the provision of a spool rotatably mounted in the hollow base, with floss being wound upon the spool and extending through the opening.

Thus, yet another feature of the invention is that the floss is retained on the dispenser for convenient access by the user.

A further feature of the present invention is the provision of means for cutting the floss on the base adjacent the opening.

Further features will become more fully apparent in the following description of the embodiments of this invention and from the appended claims.

DESCRIPTION OF THE PREFERRED EMBODIMENTS

Figure 1:
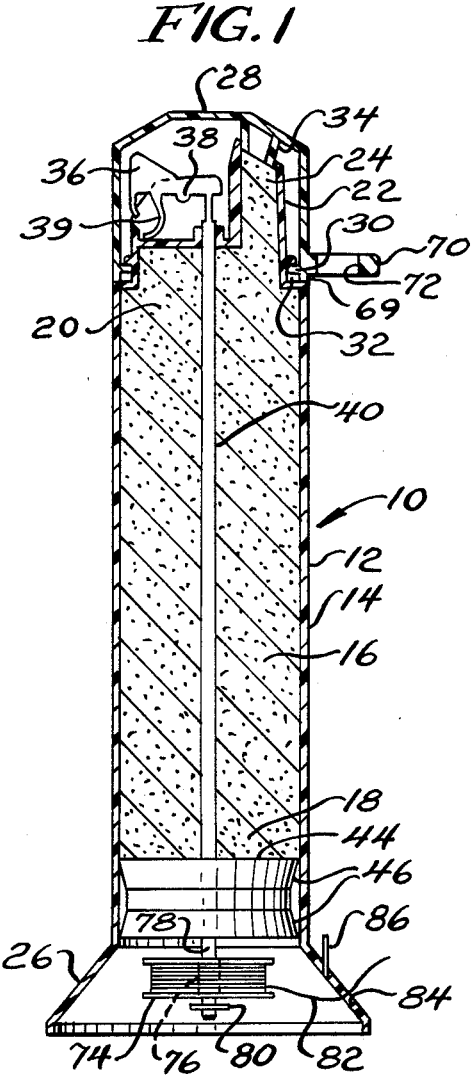
FIG. 1 is a sectional view of a dispenser of the present invention.

Referring now to FIG. 1, there is shown a dispenser generally designated 10 for pumping a flowable material, such as toothpaste, from the dispenser. The dispenser 10 has a container 12 having a cylindrical wall 14 defining an elongated chamber 16 to retain the toothpaste. The chamber 16 has a lower portion 18 and an upper portion 20. The dispenser has a nozzle 22 adjacent the upper portion 20 of the chamber 16 defining an outlet orifice 24. The dispenser 10 has an enlarged hollow base 26 for stability purposes when the dispenser is placed on a surface.

The dispenser 10 has a cap 28 which may be releasably secured to an upper portion of the container 12 by suitable means such as an inwardly directed rim 30 on a lower portion of the cap and a groove 32 in an upper portion of the container 12, with the rim 30 being received in the groove 32. The cap 28 may have an inner plug 34 which is received in the nozzle 22 in order to close the orifice 24 when the cap 28 is secured to the container 12.

Figure 2:
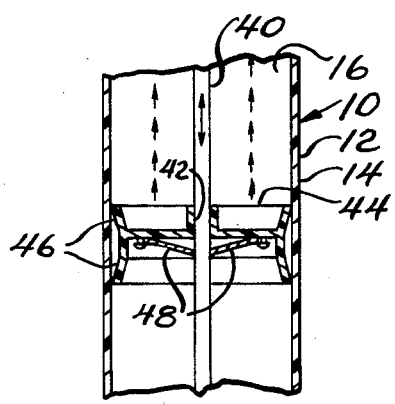
FIG. 2 is a fragmentary sectional view of a plunger for the dispenser of FIG. 1.

The dispenser 10 has a lever 36 which is pivotally mounted by a pin 38 to an upper portion of the container 12. The lever 36 has a lower arcuate spring member 39 which biases the lever upwardly in the container. An elongated rod 40 is connected to an inner portion of the pivoted lever 36. With reference to FIGS. 1 and 2, the rod 40 extends through a central opening 42 of a plunger 44 which has flanges 46 which sealingly engage against an inner surface of the wall 14. The plunger 44 may be made of a flexible material, such as plastic or rubber. The plunger 44 has a plurality of lower clips 48 made from metal which are secured to a lower portion of the plunger 44 and which engage against the rod 40. As shown, the rod 40 is received between the clips 48.

In operation, with reference to FIGS. 1 and 2, when the lever 36 is moved downwardly the rod is moved upwardly in the chamber 16, and the plunger 44 is moved upwardly slightly in the chamber 16 due to engagement of the clips 48 against the rod 40 in order to pump a small portion of material in the chamber 16 through the outlet orifice 24. However, when the lever 36 is released, the spring member 39 moves the lever 36 upwardly, and the rod moves downwardly through the plunger 44 and clips 48 while the plunger 44 remains in place. Thus, the lever 36 is repetitively moved downwardly in order to repetitively pump material from the chamber 16.

Figure 3:
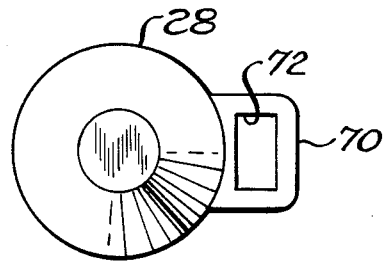
FIG. 3 is a top plan view of a cap for the dispenser.
Figure 4:
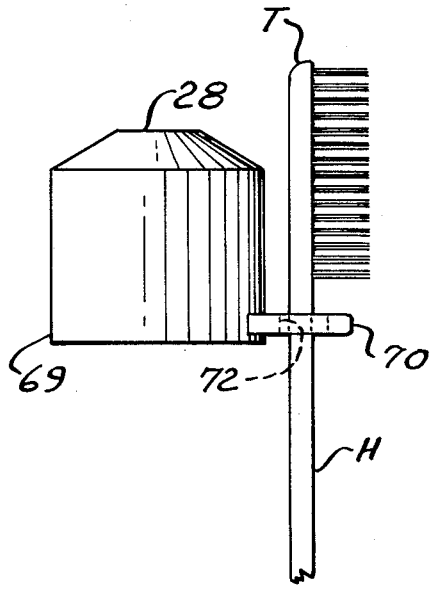
FIG. 4 is an elevational view of the cap.

With reference to FIGS. 1, 3, and 4, the cap 28 has a lower edge 69, and a tab 70 extends outwardly from a location adjacent an edge 69. The tab 70 has an elongated opening 72 extending therethrough to receive the handle H of a toothbrush T. Thus, the toothbrush T may be releasably retained in the tab 70 for convenient access and use during dispensing of the toothpaste by the dispenser 10.

With reference to FIG. 1, the dispenser 10 has a spool 74 having a central opening 76. The spool 74 is received on the rod 40 in the hollow base 26 on a lower portion 78 of the rod 40 at a location beneath the plunger 44. The opening 76 of the spool 74 is slightly larger than the rod 40, such that the spool 74 is rotatably received on the rod 40. The rod 40 has suitable means, such as a clip 80, on the rod 40 beneath the spool 74 in order to retain the spool 74 in place beneath the plunger 44 in the base 26.

An elongated strand 82 of floss is wound upon the spool 74 and extends from the spool 74 through an opening 84 in a side of the base 26, as shown. In a preferred form, the base 26 has an outwardly directed cutting member 86 adjacent the opening 84 with a sharpened edge in order to cut lengths of the floss as desired.

Thus, the dispenser 10 has a source of floss located in the dispenser 10 for convenient access, as desired, during use of the dispenser 10.

The foregoing detailed description is given for clearness of understanding only, and no unnecessary limitations should be understood therefrom, as modifications will be obvious to those skilled in the art.

I claim:
1. A dispenser, comprising:
a container having a wall defining an elongated chamber to retain a flowable material, a nozzle adjacent an upper portion of the chamber defining an outlet orifice, and a hollow base adjacent a lower portion of the container and having an opening extending through a side of the base;
an elongated rod extending longitudinally through a central portion of the chamber;
a plunger located in the chamber and sealingly engaging against an inner surface of the wall, with said rod extending through a central portion of the plunger to a location below the plunger, said plunger having clip means slidably engaging against the rod;
means for reciprocating the rod in the chamber to move the plunger upwardly in the chamber and pump a portion of the material through the orifice;
a spool rotatably received on a lower portion of the rod at a location below the plunger; and
an elongated strand of floss wound upon the spool and extending through the opening.

2. The dispenser of claim 1 wherein the container includes means for cutting the floss.

3. The dispenser of claim 2 wherein the cutting means comprises a sharp cutting member extending from a side of the base adjacent the opening.

4. The dispenser of claim 1
including
a cap having a cavity to receive the nozzle of the container, said cap having an outwardly directed tab having an opening to receive a toothbrush.

5. The dispenser of claim 4 wherein the cap has an outer edge, and in which the tab extends from a location adjacent the edge.

* * * * *